United States Patent [19]
Reinhard et al.

[11] Patent Number: 5,125,830
[45] Date of Patent: Jun. 30, 1992

[54] APPARATUS FOR AFFIXING A LIGATURE TO BRACES OF TEETH

[76] Inventors: Peter Reinhard, Winzerstrasse 6, Dietikon, Switzerland; Ulrich Hübers, Haupstrasse 5, Offenburg, Fed. Rep. of Germany

[21] Appl. No.: 617,404

[22] Filed: Nov. 21, 1990

Related U.S. Application Data

[63] Continuation of Ser. No. 355,010, May 19, 1989, abandoned.

[30] Foreign Application Priority Data

May 19, 1988 [CH] Switzerland .................. 1894/88

[51] Int. Cl.$^5$ .............................................. A61C 3/00
[52] U.S. Cl. .............................................. 433/3
[58] Field of Search ..................... 433/3, 2, 4, 159

[56] References Cited

U.S. PATENT DOCUMENTS 3,211,188 10/1965 Wallshein ........................ 433/3
3,596,357  8/1971 Matsumoto ..................... 433/3

FOREIGN PATENT DOCUMENTS 2750258  5/1979 Fed. Rep. of Germany ...... 433/159
2808149  5/1979 Fed. Rep. of Germany ........ 433/3
2481595 11/1981 France ............................. 433/3
55-32567  8/1980 Japan .

Primary Examiner—Cary E. O'Connor
Attorney, Agent, or Firm—Carl J. Evens

[57] ABSTRACT

An apparatus for correcting misalignments in human teeth comprises a rod-like member which has a grip holder for fixing a ligature wire to a brace and to brackets applied to teeth. The grip holder is connected to a rod-like tubular torsion bar arranged in the interior of a hand tube and an end tube. On the outer circumference of the torsion bar are formed threads, which cooperate via a ball cage with the threads formed on the hand tube. A rotary movement is imparted to the torsion bar and thereby the grip holder by an axial movement of the hand tube or the end tube. As a result of this rotary movement, the ends of a ligature wire inserted in the grip holder are twisted for fixing a brace guided in the bracket, and consequently the brace is fixed to the bracket for transferring the force of the brace to the teeth. Therefore fixing is sped up and simplified as compared with other fixing methods.

7 Claims, 1 Drawing Sheet

APPARATUS FOR AFFIXING A LIGATURE TO BRACES OF TEETH

This is a continuation of copending application Ser. No. 07,355,010 filed May 19, 1989, abandoned.

BACKGROUND OF THE INVENTION

The present invention relates to an apparatus and a process for fixing a bow-shaped member or brace made from wire and used for correcting misalignments of teeth in humans. In the apparatus, a brace is inserted in holding plates or brackets, of which each bracket is fixed to the labial or lingual surface of the teeth and is fixed by a ligature wire using a tool to the holding plates, as well as to the ligature wire.

In orthodontology the use of a wire brace for correcting misalignments of teeth in a so-called band brace apparatus is a known process. For this purpose brackets are fixed to the labial or lingual surface of the teeth and in same is formed a lock, in which the wire brace can be inserted. In order that the force of the brace be transferred to the teeth, it is necessary to fix the brace to the brackets. This fixing can be achieved in many different ways, e.g. by rubber rings or fine wires, the latter fastening being referred to as a ligature.

The application and fixing of such a wire brace is relatively complicated, particularly if it is necessary to correct teeth in both upper and lower jawbones.

The ligatures are formed from fine wires with a thickness of a few tenths of a millimeter, e.g. 0.2 to 0.3 mm, which are placed round the brackets and whose ends are twisted for stretching the wire. The ligature wire is placed over the brace and extends below two flaps arranged on the brackets, so that it cannot be stripped off. Fixing generally takes place with a needle holder, in which is secured a ligature wire.

A twister is known (Japanese Utility Model 1 373 903), which simplifies the application and tensioning of the ligature wires on the brackets. The twister is constructed as a rod-shaped member, on whose one end are mounted two jaws, of which one jaw is displaceable. On sliding back the one jaw, a pin is exposed, over which is placed a ligature wire in the form of a closed loop and onto which is again advanced the slid back jaw. The loop can now be placed over the bracket and the twister is manually turned until the ligature wire engages snugly on the bracket. It is then possible to slide back the jaw again and the twisted end of the loop can be removed from the pin.

In this known appliance it is necessary to obtain the twisting by turning the appliance manually. Experience has shown that roughly fifteen turns are required for a ligature, this quantity being dependent on the size of the bracket and the nature of the preshaping of the ligature wire. This relatively large number of turns involves a considerable amount of time and a large amount of physical effort.

SUMMARY OF THE INVENTION

It is an object of the present invention to provide an apparatus of the aforementioned type, in which the ligatures can be realized without assistance and which requires little time and effort for its operation.

According to the invention this and other objects of the invention are attained by an apparatus, in which on the end of a tool constructed as a rod is placed a grip holder for clamping the ends of a loop-shaped ligature wire and to which by means of a rotation mechanism housed in the interior of the rod can be applied only several turns for twisting and stretching the ligature wire placed round a bracket.

The invention also relates to a process using the inventive apparatus, in which a ligature wire is formed as a loop and with its two ends is fixed in the holding clamp of the apparatus and following application to the brackets, the ends of the wire are twisted by operating the rotation mechanism of the apparatus.

The invention also covers a ligature wire in the form of a wire loop for performing the inventive process. The wire is provided with two legs connected by a web, and in the vicinity of the webs the legs have a portion with a smaller spacing than on the connecting part, which is to be placed over the bracket. The end portions of the legs with the smaller spacing are juxtaposed.

The invention is described in greater detail hereinafter relative to an embodiment and the attached drawings.

DETAILED DESCRIPTION OF THE PREFERRED EMBODIMENTS

Figure 1:
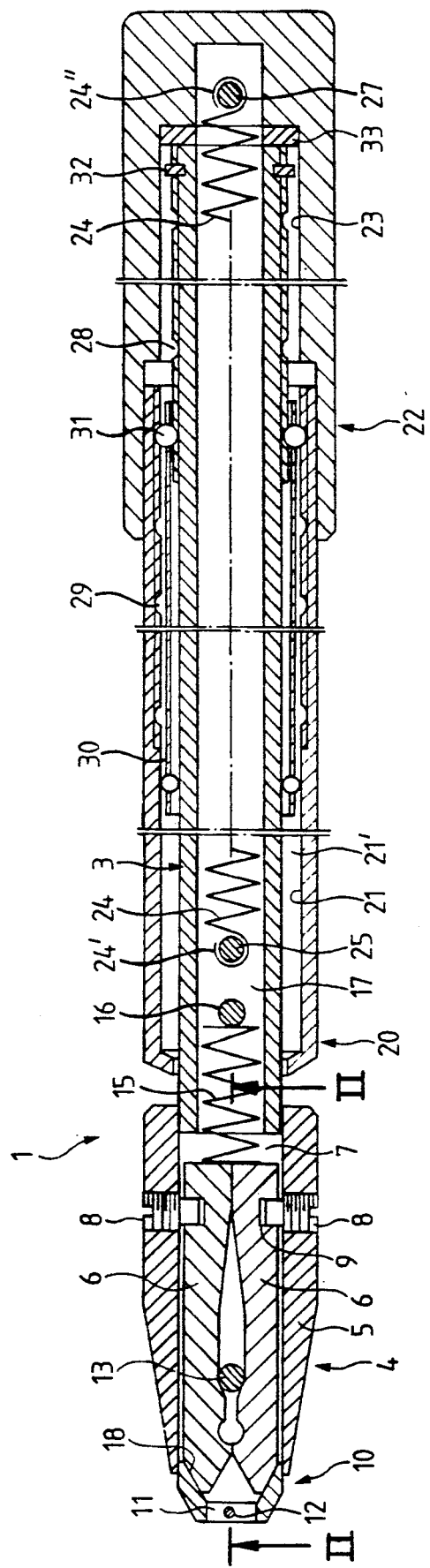
FIG. 1 is a longitudinal sectional view of an apparatus constructed in the form of a rod for applying ligature wires to brackets for fixing a brace for correcting teeth.
Figure 3:
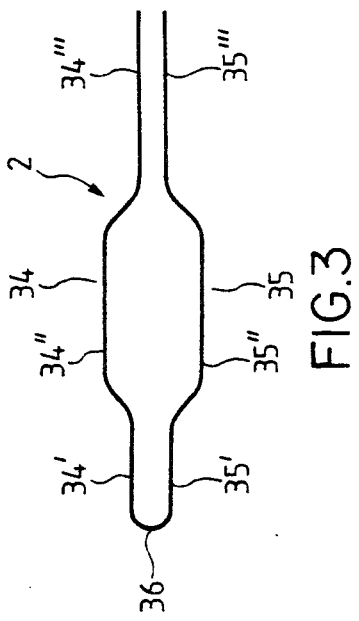
FIG. 3 is a side view of a ligature wire, which can be used with the apparatus according to FIG. 1 for fixing the brace.

An apparatus 1 shown in FIG. 1 and a ligature wire 2 shown in FIG. 3 are represented on a larger scale. Apparatus 1, which is referred to hereinafter as twister, is rod-shaped and has an inner tubular torsion bar 3 provided with a grip holder 4 mounted thereon.

The grip holder 4 comprises a sleeve 5 and two gripping jaws 6. The gripping jaws 6 are mounted in the torsion bar 3 at the end thereof. For this purpose at the end of torsion bar 3 is provided a slot 7, in which are pivotably mounted the platelet-shaped gripping jaws 6. The gripping jaws 6 are held at each of their inner ends by a threaded bolt 8, which is screwed into sleeve 5 and projects radially inwards into a depression 9 of each jaw 6.

Figure 2:
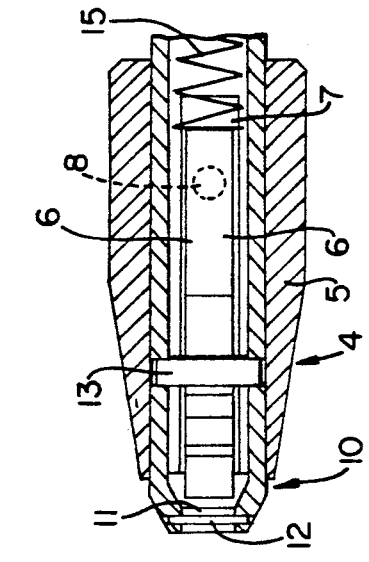
FIG. 2 is a partial side view of the apparatus shown in FIG. 1 rotated by 90 degree about the longitudinal axis of the rod.

Slot 7 in torsion bar 3 does not extend up to the end portion 10 of the torsion bar where the bar 3 is conically constructed and has an opening 11, which is traversed by a pin 12. A further pin 13 mounted in torsion bar traverses slot 7 and separates the two gripping jaws 6 from each other. FIG. 2 shows a side view of the apparatus rotated by 90 degree about the longitudinal axis of the rod, with torsion bar 3 extending to the end portion 10, and pin 13 being inserted in the torsion bar.

One end of a compression spring 15 acts on the inside ends of the gripping jaws 6, whilst its other end is supported on a bearing pin 16 mounted in the torsion bar 3 and which traverses a longitudinal bore 17 of the latter. Compression spring 15 presses the gripping jaws 6 against the inner cone of conical end portion 10, whilst exerting a clamping action. The ends of the ligature wire shown in FIG. 3 can be placed and clamped between the jaws. For inserting the ligature wire between the clamping jaws 6, sleeve 5 is slid back, so that the jaws 6 move along the pin 13 and are spread apart in accordance with the construction of their inner contour, so that the ligature wire 2 can be inserted.

The torsion bar 3 is surrounded by a sleeve-like hand tube 20, whose inner bore 21 has a larger diameter than the external diameter of bar 3, so that an annular space 21' is formed between the inner wall of hand tube 20 and the external wall of bar 3.

At its end remote from the grip holder 4, the hand tube 20 is connected to an externally closed end tube 22, whose internal diameter 23 roughly corresponds to the diameter of the inner bore 21 of hand tube 20.

The longitudinal bore 17 of torsion bar 3 is traversed by a tension spring 24, one end 24' of which is mounted in a retaining rod 25 traversing bore 17 of torsion bar 3 and the other end 24" is mounted in a retaining pin 27 mounted on the base of end tube 22. At the tube-side end of torsion bar 3 are formed threads 28 having a semicircular cross-section, whilst on the inner wall of hand tube 20 are provided corresponding threads 29 with an approximately semicircular cross-section. The threads 28 and 29 can be in one, two or multiple-thread form. The pitch of the threads 28, 29 can also vary, e.g. the pitch can increase.

Between the threads 28, 29 is mounted a ball cage 30 with balls 31 carried thereon. Cage 30 forms the connection between threads 28, 29 and causes a rotation of torsion bar 3 on displacing the hand tube 20 or end tube 22. There are only four balls 31 shown in FIG. 1, but in reality numerous balls 31 are arranged over the entire length of the ball cage 30.

At the tube-side end of torsion bar 3 is fixed a stop 32, e.g. a circlip, which limits the travel between torsion bar 3 and hand tube 20 or end tube 22. A disk 33 is inserted in the bottom of end tube 22 to damp the impact of the torsion bar 3.

The brace is fixed to brackets with the aid of the described apparatus according to FIG. 1 in the following way. After retracting sleeve 5 backwardly and inserting ligature wire 2 of FIG. 3 between jaws 6, sleeve 5 is again released, so that it slides back to the forward position shown in FIG. 1. After applying the brace for correcting the teeth, with the aid of apparatus 1 the ligature wire 2 is placed over one of the brackets, and then the hand tube 20 or end tube 22 is retracted. This leads to a rotary movement of the grip holder 4, which brings about the twisting of the ends of ligature wire 2 and simultaneously the latter is snugly placed on the brackets and, as a result the brace is fixed.

The ligature wire 2 for use with apparatus 1 is, as can be gathered from FIG. 2, constructed as a two-leg loop, whose legs 34, 35 are interconnected by a web 36. In the vicinity of web 36, the leg portions 34', 35' have a smaller spacing than in the central portion 34", 35". The end portions 34''', 35''' of legs 34, 35 are substantially parallel to one another and have a smaller spacing than the other leg portions. It is important that between the end portions of legs 34, 35 is provided a spacing which is somewhat larger than the diameter of pin 12, which is arranged in the conical end portion 10 of torsion bar 3.

As the ligature wire 2 is required in large quantities, it is generally made available by means of a dispenser or the like, which in each case supplies one ligature wire.

There has been disclosed heretofore the best embodiment of the invention presently contemplated. However, it is to be understood that various changes and modifications may be made thereto without departing from the spirit of the invention.

What is claimed is:

1. Apparatus for positioning a ligature wire to form a brace for correcting misalignments in human teeth wherein the brace formed from the wire is inserted in brackets fixed to the labial or lingual surfaces of the teeth comprising:
    a rod-shaped torsion bar with a slot near one end terminating in an opening having internal conically shaped surfaces facing the slot and threads formed in the external wall of the bar and spaced from the slot;
    a sleeve-like tube with an inner bore of a diameter larger than the external diameter of the torsion bar positioned about the torsion bar to form an annular space between the inner wall of the tube and the external wall of the bar, said inner bore of the tube having threads formed therein which correspond to the threads in the external wall of the bar;
    a ball cage with balls carried thereon positioned in the annular space between the bar and the tube, the balls being positioned in the cage so that they ride in the corresponding threads in the bar and sleeve and permit the bar and sleeve to smoothly rotate relative to each other;
    gripping jaws mounted in the slot in the bar for holding ligature wire to be inserted on the brackets on the teeth; and
    means for urging the jaws into contact with the conical surfaces of the bar to normally hold the jaws in a closed position.

2. Apparatus in accordance with claim 1, wherein means are provided for pivotally securing the jaws in the slot.

3. Apparatus in accordance with claim 2, wherein an end tube is provided which partly surrounds the sleeve-like tube and is connected to the tube, whereby upon axial displacement of either of said tubes rotary movement is imparted to said torsion bar by means of the ball cage and threads.

4. Apparatus according to claim 3, wherein said threads are single threads.

5. Apparatus according to claim 3, wherein said threads are multiple threads.

6. Apparatus according to claim 3, wherein a pin is transversely mounted in the slot in the torsion bar and extends between the gripping jaws for opening the jaws when the jaws are moved toward the pin.

7. Apparatus according to claim 1 wherein the length of the ball cage is less than the axial length of the annular space for allowing displacement of the cage in the annular space to permit rotation of the bar and sleeve relative to one another.

* * * * *